(12) United States Patent
Swaminathan et al.

(10) Patent No.: US 8,481,769 B2
(45) Date of Patent: Jul. 9, 2013

(54) ISOLATION AND PURIFICATION OF CARTENOIDS FROM MARIGOLD FLOWERS

(75) Inventors: Sethuraman Swaminathan, Bangalore (IN); Kunhiraman Priya Madavalappil, Bangalore (IN)

(73) Assignee: Katra Phytochem (India) Private Limited, Bangalore (IN)

( * ) Notice: Subject to any disclaimer, the term of this patent is extended or adjusted under 35 U.S.C. 154(b) by 498 days.

(21) Appl. No.: 12/570,684

(22) Filed: Sep. 30, 2009

(65) Prior Publication Data

US 2010/0081850 A1 Apr. 1, 2010

Related U.S. Application Data

(63) Continuation-in-part of application No. 11/667,285, filed on May 8, 2007, now Pat. No. 7,622,599.

(51) Int. Cl.
*C11B 1/10* (2006.01)
*C07C 35/21* (2006.01)

(52) U.S. Cl.
USPC ........... 554/20; 554/8; 568/816; 568/838; 424/774

(58) Field of Classification Search
None
See application file for complete search history.

(56) References Cited

U.S. PATENT DOCUMENTS

| | | | |
|---|---|---|---|
| 5,382,714 A | 1/1995 | Khachik | |
| 5,648,564 A | 7/1997 | Ausich et al. | |
| 6,380,442 B1 * | 4/2002 | Madhavi et al. | 568/816 |
| 6,504,067 B1 | 1/2003 | Montoya-Olvera et al. | |
| RE38,009 E * | 2/2003 | Garnett et al. | 424/451 |
| 6,743,953 B2 | 6/2004 | Kumar T.K. et al. | |
| 6,784,351 B2 * | 8/2004 | Hauptmann et al. | 800/323 |
| 7,173,145 B2 | 2/2007 | Khachik | |
| 2005/0038271 A1 * | 2/2005 | Khachik | 554/8 |
| 2007/0032683 A1 * | 2/2007 | Xu et al. | 568/816 |

FOREIGN PATENT DOCUMENTS

| | | |
|---|---|---|
| CN | 1120565 | 4/1996 |
| JP | 11322708 | 11/1999 |
| WO | 03048284 A1 | 6/2003 |

OTHER PUBLICATIONS

Lichtenthaler, H.K., et al., Chlorophylls and Carotenoids: measurement and characterizatin by UV-VIS spectroscopy, 2001, Current Protocols in Food Analytical Chemistry, unit F4.3, suppliment 1, pp. F4.3.1-F4.3.8.*

Naguib, Y., Carotenoids come of age, 2003, Functional Foods & Nutraceuticals, (12 pages).*
Breithaupt, D.E., et al., Lutein and zeaxanthin in new dietary supplements—analysis and quantification, 2004, vol. 220, pp. 648-652.*
Kyowa Hakko Kogyo Co. Ltd. JP 11-322708, 1999, (English translation 8 pages).
Brazana, E. et al., Enzyme-Mediated solvent Extraciton of Carotenoids form Marigold Flower (*Tagetes erecta*), 2002, Journal of Agric. Food Chem., vo. 50. No. 16, pp. 4491.
Moeller et al., "The Potential Role of Dietary Xanthophyllis in Cataract and Age-Related Macular Degeneration" Journal of the American College of Nutrition, vol. 19, No. 5, 522S-527S (2000).
Hininger et al., "No Significant Effects of Lutein, Lycopene or B-Carotene Supplementation on Biological Markers of Oxidative Stress and LDL Oxidizability in Health Adult Subjects" Journal of the American College of Nutrition, vol. 20, No. 3, 232-238 (2001).
Chopra et al., "Effect of lutein on oxidation of low-density lipoproteins (LDL) in vitro" Proceedings of the Nutrition Society, 53 p. 18A, 1993.
Britton, "Structure and properties of carotenoids in relation to function" FASEB J 9, 1551-1558 (1995).
Pfander, "Carotenoids: An Overview" Methods in Enzymology, vol. 213 (1992).
Howard et al., "Do Hydroxy-Carotenoids Prevent Coronary Heart Disease? A Comparison Between Belfast and Toulouse" Internat. J. Vit. Nut_ Res. 66, 113-118 (1996).
Chew et al., "Effects of Lutein from Marigold Extract on Immunity and Growth of mammary Tumors in Mice" Anti Cancer Research 16, 3689-3694 (1996).
Ong et al., "Natural Sources of Carotenoids from Plants and Oils" Methods in Enzymology, vol. 213 (1992).
Mercandante, "New carotenoids: Recent progress" Pure Appl. Chem., vol. 71, No. 12, pp. 2263-2272 (1999).

* cited by examiner

*Primary Examiner* — Yate K Cutliff
(74) *Attorney, Agent, or Firm* — Sughrue Mion, PLLC

(57) ABSTRACT

A process for isolation of carotenoids crystals having lutein and zeaxanthin in a weight ratio of about 10:1, 5:1 or 1:1. The process comprises contacting a plant source rich in lutein with hexane and extracting at a temperature of about 40° C. to 60° C. to obtain an oleoresin rich in lutein; contacting a plant source rich in zeaxanthin with hexane and extracting at a temperature of about 40° C. to 60° C. to obtain an oleoresin rich in zeaxanthin. The oleoresin rich in lutein and the oleoresin rich in zeaxanthin are mixed separately in a ratios ranging from about 80:20 (w/w) to 90:10 (w/w) or about 70:30 (w/w) to 30:70 (w/w) or about 10:90 (w/w) to 20:80 (w/w) and homogenized to obtain a mixed oleoresin. The mixed oleoresin is hydrolyzed with an alcoholic alkali at a temperature of about 70° C. to 80° C. to obtain a reaction mixture. The carotenoids crystals are precipitated by adding hot water to the reaction mixture to form a precipitate. Carotenoids crystals having lutein and zeaxanthin in a ratio of about 10:1 or 5:1 or 1:1 respectively are obtained by filtering, washing and drying the precipitate.

17 Claims, No Drawings

ISOLATION AND PURIFICATION OF CARTENOIDS FROM MARIGOLD FLOWERS

This is a Continuation-in-Part of application Ser. No. 11/667,285 filed May 8, 2007, which is a National Stage Application filed under §371 of PCT Application No. PCT/IN05/00123 filed Apr. 25, 2005. The entire disclosure(s) of the prior application(s), application Ser. No. 11/667,285 is considered part of the disclosure of the accompanying continuation-in-part application and is hereby incorporated by reference.

FIELD OF THE INVENTION

The present invention relates to pure carotenoid crystals derived from Marigold flowers and particularly to their isolation and purification process.

BACKGROUND OF THE INVENTION

Pure carotenoid crystals derived from Marigold flowers, comprising predominantly of Xanthophylls such as Lutein, Zeaxanthin and Cryptoxanthin and low levels of β-carotene have been proven scientifically to reduce the risk of age related macular degeneration (Reference: Moeller S M, Jacques P F, Blumberg J B "The potential role of dietary Xanthophylls in cataract and age related macular degeneration," Journal of the American College of Nutrition, 2000; 19: 522S-527S), control over LDL cholesterol (Reference: Chopra M., Thurnham D I, "Effect of Lutein on oxidation of low density lipoproteins (LDL) in vitro", Proceedings of the Nutrition Society, 1994; 53: 1993, # 18A.), prevention of Coronary heart diseases (Reference: Howard A N, Williams N R, Palmer C R, Cambou J P, Evans A E, Foote J W, et al. "Do hydroxy-carotenoids prevent coronary heart disease?" A comparison between Belfast and Toulouse. "International Journal of Vitamin and Nutrition Research, 1996; 66: 113-118) and free radicals scavenging and immunity enhancing (Reference: Chew B P, Wong M W, Wong T S, "Effects of Lutein from Marigold extract on immunity and growth of mammary tumors in mice," Anticancer Research, 1996; 16: 3689-3694).

Lutein, (β-ε-carotene-3-3'-diol) and Zeaxanthin (β-β-carotene-3-3'diol) belong to Xanthophylls group in the carotenoids family with highly reactive hydroxyl groups which cannot be synthesized by humans and animals.

Carotenoids are a class of natural fat-soluble pigments found principally in plants, algae, and photosynthetic bacteria, where they play a critical role in the photosynthetic process. They also occur in some non-photosynthetic bacteria, yeasts, and molds, where they may carry out a protective function against damage by light and oxygen. Although animals appear to be incapable of synthesizing carotenoids, many animals incorporate carotenoids from their diet. Within animals, carotenoids provide bright coloration, serve as antioxidants, and can be a source for vitamin A activity (Ong and Tee 1992: Britton et al. 1995).

Carotenoids are responsible for many of the red, orange, and yellow hues of plant leaves, fruits, and flowers, as well as the colors of some birds, insects, fish, and crustaceans. Some familiar examples of carotenoid coloration are the oranges of carrots and citrus fruits, the reds of peppers and tomatoes, and the pinks of flamingoes and salmon (Pfander 1992). Some 600 different carotenoids are known to occur naturally (Ong and Tee 1992), and new carotenoids continue to be identified (Mercadante 1999).

Carotenoids are defined by their chemical structure. The majority carotenoids are derived from a 40-carbon polyene chain, which could be considered the backbone of the molecule. This chain may be terminated by cyclic end-groups (rings) and may be complemented with oxygen-containing functional groups. The hydrocarbon carotenoids are known as carotenes, while oxygenated derivatives of these hydrocarbons are known as xanthophylls. Beta-carotene, the principal carotenoid in carrots, is a familiar carotene, while Lutein, the major yellow pigment of marigold petals, is a common xanthophyll.

The structure of a carotenoid ultimately determines what potential biological function(s) that pigment may have. The distinctive pattern of alternating single and double bonds in the polyene backbone of carotenoids is what allows them to absorb excess energy from other molecules, while the nature of the specific end groups on carotenoids may influence their polarity.

The former may account for the antioxidant properties of biological carotenoids, while the latter may explain the differences in the ways that individual carotenoids interact with biological membranes (Britton 1995).

U.S. Pat. No. 5,382,714 discloses process for isolation of pure lutein comprising from saponified marigold oleoresin containing free lutein.

U.S. Pat. No. 5,648,564 uses aqueous alkali and propylene glycol wherein the Carotenoid esters are neither soluble nor freely miscible with them and hence it requires very long time at higher temperature for the fatty esters to saponify which may result in exposure of the product for a longer duration under heat and air, promoting the formation of oxidative degenerative products and the process time is too long for a commercial batch.

U.S. Pat. No. 6,743,953 describes final purification step involving multiple solvents like ethyl acetate, hexane, acetone and methanol with the possibilities of leaving residues of the same. Again the process involves saponification upto 3 hrs. Subjecting the product to heat at 70° C. for more time which may result in degenerated oxidative, products in the saponified mass.

U.S. Pat. No. 6,380,442 states that the hydrolysis of carotenoids is done by using Iso propyl alcohol with saponification time being 90 minutes.

U.S. Pat. No. 6,504,067 states that the Marigold oleoresin is pre treated with Sodium Carbonate and further neutralisation with dilute Phosphoric acid, prior to taking it to saponification reaction using aqueous alkali and carried out the saponification at a temperature at 90° C. for 8 hours. Subsequently the reaction mass is subjected to readjustment of pH with acetic acid to 5.0, and washing the residues with excess water in order to bring the pH to neutral. The disadvantage in the process is that the product is subjected to heat for a prolonged period and too many steps of acidification and neutralisations are involved to remove the impurities.

BRIEF SUMMARY OF THE INVENTION

The present invention is realistic and effective process to isolate carotenoids, predominantly, Lutein from marigold flower petals (as the preferred source). The process involves ensilaging marigold flower petals under controlled anaerobic conditions to fix and enrich the carotenoids present in the petals, dehydration involving couple of steps like screw press, shredding and fluidised bed drying using eco friendly producer gas as heating medium for the drier without any hazardous stack emission to obtain dried meal. The dried meal is then pelletised to convenient size, density and hardness to facilitate better extractability of the carotenoid esters. The pellets are solvent extracted using food grade hexanes and are stripped for solvent to the least possible extent without much degradation in the oleoresin.

The oleoresin is then homogenized with absolute alcohol before the addition of alkali and the esters are saponified at temperature between 70° C. and 80° C. for a maximum time of 30 minutes only. The hydrolyzed carotenoids are then precipitated using a mixture of water and alcohol and washed with hot water for the removal of all unwanted trace impurities. The washed crystals are then filtered using Centrifuge and then dried either under vacuum or under atmospheric pressure to remove moisture and volatile organic impurities, if any.

The advantages of the present invention is that the carotenoid esters can be saponified within 30 minutes duration only upto more than 99% saponification and the product is not subjected to heat for a longer duration which may result in the formation of degenerated oxidative products. The saponified mass is immediately precipitated with the aid of alcohol-water mixture under slightly warm conditions aiding the removal of most of the unwanted and unreacted impurities in a single step. The whole process of homogenisation, saponification, precipitation, washing and filtration can be completed within a time span of 3 hours.

The present invention has advantage in its time—temperature combination, simplicity of procedure and usage of low amounts of solvents. All these factors contribute towards the yield and stability of the product and bring down the cost of production on a commercial scale.

An aspect of the present disclosure is a process for isolation of carotenoids crystals having lutein and zeaxanthin in a weight ratio of about 10:1, 5:1 or 1:1. The process comprises contacting a plant source rich in lutein with hexane and extracting at a temperature of about 40° C. to 60° C. to obtain an oleoresin rich in lutein; contacting a plant source rich in zeaxanthin with hexane and extracting at a temperature of about 40° C. to 60° C. to obtain an oleoresin rich in zeaxanthin. The oleoresin rich in lutein and the oleoresin rich in zeaxanthin are mixed separately in a ratio ranging from about 80:20 (w/w) to 90:10 (w/w) or about 70:30 (w/w) to 30:70 (w/w) or about 10:90 (w/w) to 20:80 (w/w) and homogenized to obtain a mixed oleoresin. The mixed oleoresin is hydrolyzed with an alcoholic alkali at a temperature of about 70° C. to 80° C. to obtain a reaction mixture. The carotenoids crystals are precipitated by adding hot water to the reaction mixture to form a precipitate. Carotenoids crystals having lutein and zeaxanthin in a ratio of about 10:1 or 5:1 or 1:1 respectively are obtained by filtering, washing and drying the precipitate.

Carotenoids crystals comprising lutein and zeaxanthin, wherein a weight ratio of the lutein to zeaxanthin is about 10:1, 5:1 or 1:1 are also aspects of the present disclosure. Carotenoid crystals with these weight ratios made by the process as described above are also part of this invention. These ratios of lutein to zeaxanthin, specifically 10:1, 5:1 or 1:1, are critical in making the carotenoids more bioactive. The carotenoids crystals comprising lutein and zeaxanthin, wherein a weight ratio of the lutein to zeaxanthin is about 10:1, 5:1 or 1:1 are useful as antioxidants. These carotenoids crystals are particularly good for eye care.

DETAILED DESCRIPTION OF THE INVENTION

The present invention is realistic and effective process to isolate and purify carotenoids from Marigold flower petals, comprising predominantly Lutein. The cultivar *Tagetes erecta* is cultivated under dedicated package of practices including seed production, harvested and brought to the dehydration unit within hours of harvest. The package of practices includes non-GMO seed development and cultivation suiting tropical conditions. The flowers are then immediately taken for silaging in silos after physical cleaning and sprayed with anti oxidant and silage additive at appropriate concentration under closed anaerobic conditions.

The silaging is monitored through pH and temperature of the silage and ensured for complete fermentation over a period of two to three weeks.

The silaged flowers are then harvested from the silos and subjected to dehydration process in series of steps. The silaged flowers are subjected to industrial screw press in two stages and are squeezed for the oozing water, bringing the moisture content from 88% to 75%. The squeezed flowers are then subjected to shredding before it is dried in fluid bed drier. The shredded flowers are dried in a fluid bed drier using hot air, generated by heating air with producer-gas flame produced by using an eco-friendly gassifier with absolutely stack free emission. The tunnel type industrial fluid bed drier comprises of drying chambers with different temperatures across the tunnel from inlet, being the maximum temperature (85° C. to 90° C.) to the outlet at temperature (45° C. to 50° C.).

The transit time inside the FBD from inlet to outlet is only 30 minutes maximum, wherein the moisture level in the product is brought down to around 10% from 75%. The advantage in this drying process is that the product is not subjected to high heat for longer duration, minimising the formation of degenerative oxidative products that could form due to heat and air for prolonged periods.

The dried Marigold meal is pulverised using an industrial hammer mill and down sized to particles less than 400 microns.

The ground Marigold meal is pelletised to 6 mm to 10 mm size pellets using an industrial pelletiser to the desired bulk density with the aid of steam/hot water as binder.

The Marigold flower pellets are subjected to solvent extraction using food grade Hexanes as solvent in a battery of extractors under counter current extraction to achieve maximum extractability of active principles viz., Xanthophylls and carotenoids along with the other resinoids and lipids. The lean miscella is then concentrated in Falling film evaporators and Wiped film evaporators to bring down the solvent concentration to around 5% from 90% to 95% approximately. The concentrated miscella is then subjected to vacuum distillation to bring down the solvent level from 5% to 1%. This crude Marigold Oleoresin with 1% solvent level in it is further concentrated by stripping the solvent under a stream of Nitrogen and Steam to reduce the solvent levels to less than 1000 ppm in the final Marigold oleoresin. Throughout the concentration operation the product is not subjected to temperatures more than 60° C. at any given point of time, minimising the formation of oxidative degenerated products like Epoxides.

The Marigold oleoresin obtained is homogenised in a reactor under stirring at a temperature not exceeding 45° C. for a period of maximum 10 minutes.

The homogenised Marigold oleoresin is then hydrolyzed in the same reactor with the addition of 1.2 to 2.0 volumes of 13% to 15% alcoholic Potassium Hydroxide solution, of the quantity of the Marigold oleoresin, at a temperature ranging between 70° C. and 80° C. for a time period of not more than 30 minutes wherein the alcohol used is absolute Ethyl alcohol with moisture content less than 5%. The degree of saponification is ensured by either Thin layer chromatography or High pressure liquid chromatography and the final cooking is done for 10 minutes at the same temperature after ensuring the completion of saponification more than 99%.

To the saponified mass, hot water generated in a separate vessel at a temperature of 65° C. to 75° C. is added and homogenised well for 10 minutes at the same temperature to aid the crystallisation of Carotenoids in the mixture of water and absolute alcohol in the ratio of 1:1, wherein the ratio of Ethyl alcohol to water at 50:50, prothotes better crystallisation of Carotenoids and as well dissolves the unwanted impurities like soaps, lipids, fats and other organic matters.

The diluted mass is then filtered through a filter press by pumping the mass into the filter press aided by positive pressure using either Nitrogen or air. The collected mass inside the filter press plate is given with a hot water wash at a temperature of 60° C. to 70° C. with sufficient quantity of hot water until the pH is brought down to neutral at around 7.0.

The wet mass collected from the filter press is taken in trays in thin layers and dried in tray drier at a temperature between 50° C. and 55° C. at atmospheric pressure or in a vacuum tray drier at reduced pressure at a temperature between 40° C. and 45° C. for the time (usually 3 to 4 hours) until the moisture level in the product is less than 1% and any hazardous organic volatile impurity is below the detectable limit determined by Gas chromatography.

The resulting product contains a minimum of 90% Carotenoids determined by spectrophotometer and contains a minimum of 90% all trans-Lutein, 5 to 8% all trans-Zeaxanthin, less than 1% each of cis-Luteins, Beta carotene and Cryptoxanthin, determined by normal phase High pressure liquid chromatography.

The chemical recovery of the active principles viz., Carotenoids and Xanthophylls in the end product is between 55% and 80% depending upon the desired final product purity and the variable conditions thereof utilised based on the above process parameters by slight modifications of the process herein.

The finished product of carotenoid crystals obtained are formulated and stabilised in bulk, in the form of Powder, Beadlets, Granules, Oil dispersions and Water dispersions with concentrations varying from 1% to 40% concentrations by adding suitable pharma grade excipients and emulsifiers depending upon the end usage in line with the nutraceutical and food products applications.

Conventional methods for preparing the carotenoid crystals having both lutein and zeaxanthin, such as crystal blending after purifying lutein crystals and zeaxanthin crystals individually, results in varied ratios of lutein and zeaxanthin. Further, with such methods the recoveries of zeaxanthin purified crystals obtained is very low which is not economical on a commercial scale. Thus, there is also a need for a process for isolation of carotenoids crystals rich in lutein and zeaxanthin from plant sources, to obtain carotenoids crystals of lutein and zeaxanthin in the ratios of about 10:1, about 5:1 and about 1:1.

An alternate embodiment of the disclosure provides carotenoids crystals comprising lutein and zeaxanthin in the ratios of about 10:1, 5:1 or 1:1. The present disclosure also provides an alternate embodiment of the process for isolation of carotenoids crystals having lutein and zeaxanthin in the ratios of about 10:1, 5:1 and 1:1. It comprises contacting a plant source rich in lutein with hexane and extracting at a temperature in the range of about 40° C. to 60° C. to obtain an oleoresin rich in lutein. A plant source rich in zeaxanthin is extracted with hexane at a temperature in the range of about 40° C. to 60° C. to obtain an oleoresin rich in zeaxanthin. The oleoresin rich in lutein is mixed with the oleoresin rich in zeaxanthin separately in ratios ranging from about 80:20 (w/w) to 90:10 (w/w), or about 70:30 (w/w) to 30:70 (w/w) or about 10:90 (w/w) to 20:80 (w/w). The mixed oleoresin is hydrolyzed with an alcoholic alkali at a temperature in the range of about 70° C. to 80° C. to obtain a reaction mixture. Carotenoids crystals are precipitated by adding hot water to the reaction mixture, wherein ratio of reaction mixture to the hot water is in the range of about 1:1 to 1:1.5 (v/v). Carotenoids crystals having lutein and zeaxanthin in a ratio of about 10:1, 5:1 and 1:1 respectively are obtained by filtering, washing and drying the precipitate.

In an embodiment the present disclosure provides carotenoids crystals comprising lutein and zeaxanthin, wherein a weight ratio of the lutein to zeaxanthin is about 10:1.

In another embodiment the present disclosure provides carotenoids crystals comprising lutein and zeaxanthin, wherein a weight ratio of the lutein to zeaxanthin is about 5:1.

In another embodiment the present disclosure provides carotenoids crystals comprising lutein and zeaxanthin, wherein a weight ratio of the lutein to zeaxanthin is about 1:1.

Yet another embodiment of the present disclosure provides a process for isolation of carotenoids crystals having lutein and zeaxanthin in a weight ratio of about 10:1, said process comprising; contacting a plant source rich in lutein with hexane and extracting at a temperature of about 40° C. to 60° C. to obtain an oleoresin rich in lutein; contacting a plant source rich in zeaxanthin with hexane and extracting at a temperature of about 40° C. to 60° C. to obtain an oleoresin rich in zeaxanthin; mixing the oleoresin rich in lutein and the oleoresin rich in zeaxanthin in a ratio ranging from about 80:20 (w/w) to 90:10 (w/w) and homogenizing to obtain a mixed oleoresin; hydrolyzing the mixed oleoresin with an alcoholic alkali at a temperature of about 70° C. to 80° C. to obtain a reaction mixture; precipitating carotenoids crystals by adding hot water to the reaction mixture to form a precipitate; and obtaining carotenoids crystals having lutein and zeaxanthin in a ratio of about 10:1. The carotenoids crystals having lutein and zeaxanthin in a ratio of about 10:1 are obtained by filtering, washing and drying the precipitate.

Yet another embodiment of the present disclosure provides a process for isolation of carotenoids crystals having lutein and zeaxanthin in a weight ratio of about 10:1, wherein the plant source is selected from the group consisting of Marigold flowers, Marigold petals, mutant Marigold flowers, mutant Marigold petals, fruits of paprika and berries of Chinese wolfberries (*Lycium barbarum*). The plants particularly suited to the above process include but are not limited to natural Marigold (*Tagetes erecta*), mutated marigold, Paprika and Chinese wolfberries (*Lycium Barbarum*)

Yet another embodiment of the present disclosure provides a process for isolation of carotenoids crystals having lutein and zeaxanthin in a weight ratio of about 10:1, wherein the alcoholic alkali is selected from the group consisting of ethanolic sodium hydroxide and ethanolic potassium hydroxide.

Yet another embodiment of the present disclosure provides a process for isolation of carotenoids crystals having lutein and zeaxanthin in a weight ratio of about 10:1, wherein the alcoholic alkali is 10%-30%.

Yet another embodiment of the present disclosure provides a process for isolation of carotenoids crystals having lutein and zeaxanthin in a weight ratio of about 10:1, wherein the alcoholic alkali is 10%-30% ethanolic potassium hydroxide.

Yet another embodiment of the present disclosure provides a process for isolation of carotenoids crystals having lutein and zeaxanthin in a weight ratio of about 10:1, wherein, ratio of the reaction mixture to the hot water is in the range of about 1:1 to 1:1.5 (v/v). Yet another embodiment of the present disclosure provides a process for isolation of carotenoids crystals having lutein and zeaxanthin in a weight ratio of about 10:1, wherein the washing is carried out with hot water at a temperature in the range of about 55° C. to 80° C.

Yet another embodiment of the present disclosure provides a process for isolation of carotenoids crystals having lutein and zeaxanthin in a weight ratio of about 10:1, wherein the washing is carried out at about 75° C.

Yet another embodiment of the present disclosure provides a process for isolation of carotenoids crystals having lutein and zeaxanthin in a weight ratio of about 10:1, wherein the drying of carotenoids crystals is carried out at a temperature in the range of about 55° C. to 60° C.

Yet another embodiment of the present disclosure provides a process for isolation of carotenoids crystals having lutein and zeaxanthin in a ratio of about 5:1, said process comprising: contacting a plant source rich in lutein with hexane and extracting at a temperature of about 40° C. to 60° C. to obtain an oleoresin rich in lutein; contacting a plant source rich in zeaxanthin with hexane and extracting at a temperature of about 40° C. to 60° C. to obtain an oleoresin rich in zeaxanthin; mixing the oleoresin rich in lutein and the oleoresin rich in zeaxanthin in a ratio ranging from about 70:30 (w/w) to 30:70 (w/w) and homogenizing to obtain a mixed oleoresin; hydrolyzing the mixed oleoresin with an alcoholic alkali at a temperature of about 70° C. to 80° C. to obtain a reaction mixture; precipitating carotenoids crystals by adding hot water to the reaction mixture to form a precipitate; and (1:4 volumes is the ratio of the oleoresin to water which corresponds to about 1:1.4 volumes calculated to ratio of the reaction mixture to water) obtaining carotenoids crystals having lutein and zeaxanthin in a ratio of about 5:1. The carotenoids crystals having lutein and zeaxanthin in a ratio of about 5:1 are obtained by filtering, washing and drying the precipitate.

Yet another embodiment of the present disclosure provides a process for isolation of carotenoids crystals having lutein and zeaxanthin in a weight ratio of about 5:1, wherein the plant source is selected from the group consisting of Marigold flowers, Marigold petals, mutant Marigold flowers, mutant Marigold petals, fruits of paprika and berries of Chinese wolfberries (*Lycium barbarum*). The plants particularly suited to the above process include but are not limited to natural Marigold (*Tagetes erecta*), mutated marigold, Paprika and Chinese wolfberries (*Lycium Barbarum*)

Yet another embodiment of the present disclosure provides a process for isolation of carotenoids crystals having lutein and zeaxanthin in a weight ratio of about 5:1, wherein the alcoholic alkali is selected from the group consisting of ethanolic sodium hydroxide and ethanolic potassium hydroxide.

Yet another embodiment of the present disclosure provides a process for isolation of carotenoids crystals having lutein and zeaxanthin in a weight ratio of about 5:1, wherein the alcoholic alkali is 10%-30%.

Yet another embodiment of the present disclosure provides a process for isolation of carotenoids crystals having lutein and zeaxanthin in a weight ratio of about 5:1, wherein the alcoholic alkali is 10%-30% ethanolic potassium hydroxide.

Yet another embodiment of the present disclosure provides a process for isolation of carotenoids crystals having lutein and zeaxanthin in a weight ratio of about 5:1, wherein ratio of the reaction mixture to the hot water is in the range of about 1:1 to 1:1.5 (v/v). Yet another embodiment of the present disclosure provides a process for isolation of carotenoids crystals having lutein and zeaxanthin in a weight ratio of about 5:1, wherein the washing is carried out with hot water at a temperature in the range of about 55° C. to 80° C.

Yet another embodiment of the present disclosure provides a process for isolation of carotenoids crystals having lutein and zeaxanthin in a weight ratio of about 5:1, wherein the washing is carried out at about 75° C.

Yet another embodiment of the present disclosure provides a process for isolation of carotenoids crystals having lutein and zeaxanthin in a weight ratio of about 5:1, wherein the drying of carotenoids crystals is carried out at a temperature in the range of about 55° C. to 60° C.

Yet another embodiment of the present disclosure provides a process for isolation of carotenoids crystals having lutein and zeaxanthin in a ratio of about 1:1, said process comprising: contacting a plant source rich in lutein with hexane and extracting at a temperature of about 40° C. to 60° C. to obtain an oleoresin rich in lutein; contacting a plant source rich in zeaxanthin with hexane and extracting at a temperature of about 40° C. to 60° C. to obtain an oleoresin rich in zeaxanthin; mixing the oleoresin rich in lutein and the oleoresin rich in zeaxanthin in a ratio ranging from about 10:90 (w/w) to 20:80 (w/w) and homogenizing to obtain a mixed oleoresin; hydrolyzing the mixed oleoresin with an alcoholic alkali at a temperature of about 70° C. to 80° C. to obtain a reaction mixture; precipitating carotenoids crystals by adding hot water to the reaction mixture to form a precipitate; and obtaining carotenoids crystals having lutein and zeaxanthin in a ratio of about 1:1. The carotenoids crystals having lutein and zeaxanthin in a ratio of about 1:1 are obtained by filtering, washing and drying the precipitate.

Yet another embodiment of the present disclosure provides a process for isolation of carotenoids crystals having lutein and zeaxanthin in a ratio of about 1:1, wherein the plant source is selected from the group consisting of Marigold flowers, Marigold petals, mutant Marigold flowers, mutant Marigold petals, fruits of paprika, and berries of Chinese wolfberries (*Lycium barbarum*). The plants particularly suited to the above process include but are not limited to natural Marigold (*Tagetes erecta*), mutated marigold, Paprika and Chinese wolfberries (*Lycium Barbarum*)

Yet another embodiment of the present disclosure provides a process for isolation of carotenoids crystals having lutein and zeaxanthin in a ratio of about 1:1, wherein the alcoholic alkali is selected from the group consisting of ethanolic sodium hydroxide and ethanolic potassium hydroxide.

Yet another embodiment of the present disclosure provides a process for isolation of carotenoids crystals having lutein and zeaxanthin in a ratio of about 1:1, wherein the alcoholic alkali is 10%-30%.

Yet another embodiment of the present disclosure provides a process for isolation of carotenoids crystals having lutein and zeaxanthin in a ratio of about 1:1, wherein the alcoholic alkali is 10%-30% ethanolic potassium hydroxide.

Yet another embodiment of the present disclosure provides a process for isolation of carotenoids crystals having lutein and zeaxanthin in a ratio of about 1:1, wherein ratio of reaction mixture to the hot water is in the range of about 1:1 to 1:1.5 (v/v).

Yet another embodiment of the present disclosure provides a process for isolation of carotenoids crystals having lutein and zeaxanthin in a ratio of about 1:1, wherein the washing is carried out with hot water at a temperature in the range of about 55° C. to 80° C.

Yet another embodiment of the present disclosure provides a process for isolation of carotenoids crystals having lutein and zeaxanthin in a ratio of about 1:1 wherein the washing is carried out at about 75° C.

Yet another embodiment of the present disclosure provides a process for isolation of carotenoids crystals having lutein and zeaxanthin in a ratio of about 1:1, wherein the drying of carotenoids crystals is carried out at a temperature in the range of about 55° C. to 60° C.

Yet another embodiment of the present disclosure provides carotenoids crystals having lutein and zeaxanthin in a weight ratio of about 10:1, made by a process comprising: contacting a plant source rich in lutein with hexane and extracting at a temperature of about 40° C. to 60° C. to obtain an oleoresin rich in lutein; contacting a plant source rich in zeaxanthin with hexane and extracting at a temperature of about 40° C. to 60° C. to obtain an oleoresin rich in zeaxanthin; mixing the oleoresin rich in lutein and the oleoresin rich in zeaxanthin in a ratio ranging from about 80:20 (w/w) to 90:10 (w/w) and homogenizing to obtain a mixed oleoresin; hydrolyzing the mixed oleoresin with an alcoholic alkali at a temperature of about 70° C. to 80° C. to obtain a reaction mixture; precipitating carotenoids crystals by adding hot water to the reaction mixture to form a precipitate; and obtaining carotenoids crystals having lutein and zeaxanthin in a ratio of about 10:1. The carotenoids crystals having lutein and zeaxanthin in a ratio of about 10:1 are obtained by filtering, washing and drying the precipitate.

Yet another embodiment of the present disclosure provides carotenoids crystals having lutein and zeaxanthin in a weight ratio of about 5:1, made by a process comprising: contacting a plant source rich in lutein with hexane and extracting at a temperature of about 40° C. to 60° C. to obtain an oleoresin rich in lutein; contacting a plant source rich in zeaxanthin with hexane and extracting at a temperature of about 40° C. to 60° C. to obtain an oleoresin rich in zeaxanthin; mixing the oleoresin rich in lutein and the oleoresin rich in zeaxanthin in a ratio ranging from about 70:30 (w/w) to 30:70 (w/w) and homogenizing to obtain a mixed oleoresin; hydrolyzing the mixed oleoresin with an alcoholic alkali at a temperature of about 70° C. to 80° C. to obtain a reaction mixture; precipitating carotenoids crystals by adding hot water to the reaction mixture to form a precipitate; and obtaining carotenoids crystals having lutein and zeaxanthin in a ratio of about 5:1. The carotenoids crystals having lutein and zeaxanthin in a ratio of about 5:1 are obtained by filtering, washing and drying the precipitate.

Yet another embodiment of the present disclosure provides carotenoids crystals having lutein and zeaxanthin in a weight ratio of about 1:1, made by a process comprising: contacting a plant source rich in lutein with hexane and extracting at a temperature of about 40° C. to 60° C. to obtain an oleoresin rich in lutein; contacting a plant source rich in zeaxanthin with hexane and extracting at a temperature of about 40° C. to 60° C. to obtain an oleoresin rich in zeaxanthin; mixing the oleoresin rich in lutein and the oleoresin rich in zeaxanthin in a ratio ranging from about 10:90 (w/w) to 20:80 (w/w) and homogenizing to obtain a mixed oleoresin; hydrolyzing the mixed oleoresin with an alcoholic alkali at a temperature of about 70° C. to 80° C. to obtain a reaction mixture; precipitating carotenoids crystals by adding hot water to the reaction mixture to form a precipitate; and obtaining carotenoids crystals having lutein and zeaxanthin in a ratio of about 1:1. The carotenoids crystals having lutein and zeaxanthin in a ratio of about 1:1 are obtained by filtering, washing and drying the precipitate.

While the invention has been described with reference to the explained embodiment, it is not limiting to anybody's skill to make various changes or equivalents without altering or departing from the main scope of this invention. Therefore, it is intended that the invention not be limiting to the embodiment described but will cover and include all other embodiments falling within the scope of the claims made herein.

The following examples are illustrative, but not limiting, of the methods and compositions of the present invention. Other suitable modifications and adaptations of the variables of the conditions and normally encountered in natural products isolation and purification techniques which are obvious to those skilled in the art are within the sprit and scope of the present invention.

EXAMPLE 1

25 Kgs of Marigold Oleoresin having 92.19 gm/Kg or 9.22% of Xanthophylls is taken in 100 liters capacity reactor with an agitator. The Oleoresin is homogenised for 10 minutes under stirring at a temperature of about 40° C. with either steam or hot water in the jacket of the reactor as heating medium. Ethanolic KOH is prepared by taking 5 Kgs of KOH with purity of 95% and dissolving it in 35 liters of Ethyl alcohol (1:1.4 volumes). The prepared ethanolic KOH is added into reaction vessel slowly, containing the homogenised mass. The saponification reaction is carried out at a temperature of about 75° C. for 30 minutes. After ensuring the degree of saponification to be more than 99% by HPLC, 40 liters of demineralised hot water maintained at a temperature of 70° C. is added to the reacted mass and the stirring is continued for 10 minutes. The diluted mass with carotenoid crystals is then pumped into a filter press to recover the crystals. Around 250 liters of additional hot water is pumped through the filter press to wash the unwanted impurities and bring down the pH of the effluent to neutral around 7.0. After ensuring the neutralisation, positive pressure of Nitrogen is applied to the filter press at pressure 1.25 Kg to squeeze the crystals trapped inside the filter. The wet crystals are then collected from the filter press plates into trays in a thin layer and dried in a tray drier at a temperature around 55° C. for 3 hours under normal pressure.

The physical recovery of the final product is 6.76%. The Carotenoid crystals obtained contained 91.28% carotenoids (determined by spectrophotometer) of which 91.99% is all trans-Lutein, 6.90% all trans-Zeaxanthin, 0.27% cis-Luteins, 0.23% Beta Carotene and 0.5% Cryptoxanthin (determined by HPLC). The chemical recovery of the final product is 66.9%.

The final product contained a moisture content of 0.57% and could not be detected for any traces of residual hexanes by gas chromatography analysis.

EXAMPLE 2

25.5 Kgs of Marigold Oleoresin having 102.18 gm/Kg or 10.22% of Xanthophylls is taken in 100 liters capacity reactor with an agitator.

The Oleoresin is homogenised for 10 minutes under stirring at a temperature of about 45° C. with either steam or hot water in the jacket of the reactor as heating medium. Ethanolic KOH is prepared by taking 5.1 Kgs of KOH with purity of 95% and dissolving it 40 liters of Ethyl alcohol (1:1.56 volumes).

The prepared Ethanolic KOH is added into reaction vessel slowly, containing the homogenised mass. The saponification reaction is carried out at a temperature of 73° C. for 30 minutes. After ensuring the degree of saponification to be more than 99% by HPLC, 45 liters of demineralised hot water maintained at a temperature of about 65° C. is added to the reacted mass and the stirring is continued for 10 minutes. The diluted mass with carotenoid crystals is then pumped into a filter press to recover the crystals. Around 275 liters of additional hot water is pumped through the filter press to wash the unwanted impurities and bring down the pH of the effluent to neutral around 7.0. After ensuring the neutralisation, positive pressure of Nitrogen is applied to the filter press at pressure 1.2 Kg to squeeze the crystals trapped inside the filter. The wet crystals are then collected from the filter press plates into trays in a thin layer and dried in a tray drier at a temperature around 45° C. for 2 hours under vacuum at 600 mm Hg.

The physical recovery of the final product is 7.67%. The Carotenoid crystals obtained contained 93.76% carotenoids (determined by spectrophotometer) of which 92.86% is all trans-Lutein. 6.14% all trans-Zeaxanthin. 0.12% cis-Luteins, 0.22% Beta Carotene and 0.52% Cryptoxanthin (determined by HPLC). The chemical recovery of the final product is 70.53%.

The final product contained a moisture content of 0.63% and could not be detected for any traces of residual hexanes by gas chromatography analysis.

EXAMPLE 3

20 kg of lutein rich Marigold meal having 8.99 gm/Kg (0.89%) of total carotenoids (with a carotenoids profile of 74.58% trans-lutein (T-lutein), 4.28% trans-zeaxanthin, 1.94% of beta-carotene, 1.02% of cryptoxanthin and 18.08% cis-isomers & epoxides measured by HPLC) was taken in a 200 Liters capacity extractor with circulation facility. 120 Liters of Food grade hexane with a Gas chromatographic purity of more than 98%, was added to the extractor and circulated. The temperature was raised to about 55° C. and maintained for 1 hour, under circulation. After 1 hour the extract was drained and collected in a miscela tank. The extraction was repeated for two more times each with 120 Liters of Hexane under the same conditions of temperature and time. The extracts obtained were collected in the miscela tank. The fourth and fifth extractions were carried out using 100 Liters of hexane in each extraction under circulation and at a temperature of 58° C. 512 Liters of miscela collected from the five extractions was taken to an evaporator, preferably a falling film evaporator or a wiped film evaporator to obtain a concentrated miscela containing 70% solids and 30% solvent. The concentrated miscela was distilled further in a distillation unit under atmospheric pressure to increase the concentration of solids to 95% with a solvent level of around 5%. The solvent was distilled further under reduced pressure (450 to 600 mm Hg) to reduce the solvent level further to less than 1%. The total amount of solvent recovered was 472 Liters with a gas chromatographic purity of more than 98%. 1.624 kg of oleoresin containing 105.3 g/kg of carotenoids (10.53% carotenoids) was obtained with a carotenoids chemical recovery of 95.11%. The oleoresin thus obtained exhibited a carotenoids profile containing 74.82% trans-lutein, 5.43% T-zeaxanthin, 1.56% of betacarotene, 0.80% of cryptoxanthin and 17.38% of cis-isomers/epoxides measured by HPLC.

EXAMPLE 4

20 kg of zeaxanthin rich Marigold meal (obtained from Ball Horticulture Inc covered by the U.S. Pat. No. 6,784,351) having 3.29 g/kg (0.329%) of total carotenoids with a carotenoid profile of 59.08% T-zeaxanthin, 14.80% of betacarotene, 11.77% of T-lutein, 2.76% of alpha-cryptoxanthin, 2.33% of beta-cryptoxanthin, 1.98% of alpha-carotene, 0.82% of cis-Lutein, 0.22% of chrysanthemaxanthin and 6.24% of other unidentified carotenoids, measured by HPLC was taken in a 200 Liters capacity extractor with circulation facility. 120 Liters of Food grade hexane with a Gas chromatographic purity of more than 98%, was added to the extractor and circulated. The temperature was raised to about 45° C. and maintained for 1 hour under circulation. After 1 hour, the extract was drained and collected in a miscella tank. The extraction was repeated for 3 more times with 60 Liters of Hexane under the same conditions of temperature and time. The extracts obtained were collected in the miscella tank. 255 Liters of miscella collected from the above 4 extractions was taken to an evaporator, preferably a falling film evaporator or a wiped film evaporator to obtain a concentrated miscella containing 70% solids and 30% solvent. The concentrated miscella was distilled further in a distillation unit under atmospheric pressure to increase the concentration of solids to 95% with a solvent level of around 5%. The solvent was distilled further under reduced pressure (450 to 600 mm Hg) to reduce the solvent level further to less than 1%. The total amount of solvent recovered was 218.8 Liters with Gas chromatographic purity of more than 98%. 1.592 kg of oleoresin containing 41.26 g/kg of total carotenoids (4.126% of total carotenoids) was obtained with a recovery of 99.82%. The zeaxanthin chemical recovery was 92.07%. The oleoresin thus obtained exhibited a carotenoids profile containing 54.49% of T-zeaxanthin, 9.83% of betacarotene, 22.74% of T-lutein, 3.07% of alpha-cryptoxanthin, 1.93% of beta-cryptoxanthin, 2.75% of alpha-carotene, 0% of cis-lutein and 0.07% of chrysanthemaxanthin and 5.12% of other unidentified carotenoids, measured by HPLC.

EXAMPLE 5

The lutein rich marigold oleoresin obtained from Example 3 and the zeaxanthin rich Marigold oleoresin obtained from Example 4 are blended in the ratio of 86:14 by physical weight, respectively. 0.45 kg of blended Marigold oleoresin containing 96.28 g/kg of carotenoids (9.63% carotenoids) was homogenized for around 10 minutes in a 5.0 Liters capacity 3 necked round bottom flasks under continuous stirring at a temperature of about 40° C. in a hot water bath. Alcoholic KOH was prepared by taking 90 g of KOH (20% calculated to the input Oleoresin) with the purity of around 90% and dissolving it in 675 ml (1:1.5 volumes to the Oleoresin) of ethanol. The prepared alcoholic KOH was slowly added into reaction vessel containing the homogenized Marigold oleoresin. The saponification reaction was carried out at a temperature of about 75° C. for 30 minutes. After ensuring the degree of saponification to be more than 99% by HPLC, 1800 ml of demineralised hot water (1:4 volumes is the ratio of the oleoresin to water which corresponds to about 1:1.4 volumes calculated to ratio of the reaction mixture to water) maintained at a temperature of about 75° C. was added to the saponified Marigold oleoresin and stirring was continued for about 10 minutes. The diluted Saponified Marigold oleoresin comprising carotenoid crystals was filtered in a buchner funnel to recover the carotenoid crystals. The carotenoid crystals thus obtained were washed with 3600 ml (1:8 volumes calculated to the oleoresin) of hot water maintained at around 75° C. to remove the impurities and bring down the pH of the effluent to neutral around 7.0. The wet crystals were then collected from the filter and dried in a Fluid bed drier at a temperature of around 55° C. for 1 hour or until the moisture level is brought to less than 0.3% and the hexane and alcohol levels are less than 10 ppm and 100 ppm respectively.

36.81 g of purified carotenoids crystals rich in T-lutein and T-zeaxanthin were obtained and the physical recovery of the final product was 8.18%. The carotenoid crystals thus obtained contained 91.39% total carotenoids determined by UV-Visible spectrophotometer of which 89.84% was all T-Lutein, 9.04% all T-zeaxanthin, 0.43% beta-cryptoxanthin, and 0.37% of beta-carotene and without any traces of cis-luteins and epoxides, determined by HPLC.

The carotenoids crystals thus obtained contain 82.10% of T-lutein by weight and 8.26% by weight of T-zeaxanthin with the ratio of T-lutein to T-zeaxanthin by weight to be at about 10:1 ratio (9.94).

The carotenoid crystals thus obtained contained 8.06% of wax content when measured using Gas Chromatography. The carotenoids chemical recovery of the final product was 77.63% with a lutein chemical recovery of 97.2% and a zeaxanthin chemical recovery of 92.4%. The final product contained a moisture content of 0.29% with 68.78 ppm of ethanol and 2.36 ppm of hexanes detected by Gas chromatography.

EXAMPLE 6

The lutein rich Marigold oleoresin obtained in Example 3 and the zeaxanthin rich Marigold oleoresin obtained in Example 4 are blended in the ratio of 50:50 by physical weight, respectively. 0.45 kg of blended Marigold oleoresin containing 73.88 g/kg of carotenoids (7.388%) carotenoids was homogenized for 10 minutes in a 5.0 Liters capacity 3 necked round bottom flasks under continuous stirring at a temperature of 40° C. in a hot water bath. Alcoholic KOH was prepared by taking 90 g of KOH (20% calculated to the input oleoresin) with the purity of around 90% and dissolving it in 615 ml (1:1.5 volumes to the oleoresin) of ethanol. The prepared alcoholic KOH was slowly added into reaction vessel containing the homogenized Marigold oleoresin. The saponification reaction was carried out at a temperature of about 75° C. for 30 minutes. After ensuring the degree of saponification to be more than 99% by HPLC, 1800 ml of demineralised hot water (1:4 volumes is the ratio of the oleoresin to water which corresponds to about 1:1.4 volumes calculated to ratio of the reaction mixture to water) maintained at a temperature of about 75° C. was added to the saponified Marigold oleoresin and stirring was continued for 10 minutes. The diluted saponified Marigold oleoresin comprising carotenoid crystals was filtered in a buchner funnel to recover the carotenoid crystals. The carotenoid crystals thus obtained were washed with 3600 ml (1:8 volumes calculated to the oleoresin) of hot water maintained at around 75° C. to remove the impurities and bring down the pH of the effluent to neutral around 7.0. The wet crystals were then collected from the filter and dried in a fluid bed drier at a temperature of around 55° C. for 1 hour or until the moisture level is brought to less than 0.3% and the hexane and alcohol levels are less than 10 ppm and 100 ppm, respectively.

27.45 g of purified carotenoids crystals rich in T-lutein and T-zeaxanthin were obtained and the physical recovery of the final product was 6.1%. The carotenoid crystals thus obtained contained 90.71% total carotenoids determined by UV-Visible spectrophotometer of which 81.80% was all T-lutein, 16.2% all T-zeaxanthin, 0.69% beta-cryptoxanthin, and 0.95% of beta-carotene and without any traces of cis-luteins and epoxides, determined by HPLC.

The carotenoids crystals thus obtained contain 74.2% of T-lutein by weight and 14.69% by weight of T-zeaxanthin with the ratio of T-lutein to T-zeaxanthin by weight to be at about 5:1 ratio (5.05).

The carotenoid crystals thus obtained contained 9.20% of wax content when measured using Gas Chromatography. The carotenoids chemical recovery of the final product was 74.89% with a lutein chemical recovery of 79.99% and a zeaxanthin chemical recovery of 83.20%. The final product contained a moisture content of 0.30% with 40.30 ppm of ethanol and 6.86 ppm of hexanes detected by gas chromatography.

EXAMPLE 7

The lutein rich Marigold oleoresin obtained in Example 3 and the zeaxanthin rich Marigold oleoresin obtained in Example 4 are blended in the ratio of 15:85 by physical weight, respectively. 0.45 kg of blended Marigold oleoresin containing 51.27 g/kg of carotenoids 5.12% carotenoids) was homogenized for about 10 minutes in a 5.0 Liters capacity 3 necked round bottom flask under continuous stirring at a temperature of 40° C. in a hot water bath. Alcoholic KOH was prepared by taking 90 g of KOH (20% calculated to the input oleoresin) with the purity of around 90% and dissolving it in 675 ml (1:1.5 volumes to the oleoresin) of ethanol. The prepared alcoholic KOH was slowly added into reaction vessel containing the homogenized Marigold Oleoresin. The saponification reaction was carried out at a temperature of about 75° C. for 30 minutes. After ensuring the degree of saponification to be more than 99% by HPLC, 1800 ml of de-mineralized hot water (1:4 volumes is the ratio of the oleoresin to water which corresponds to about 1:1.4 volumes calculated to ratio of the reaction mixture to water) maintained at a temperature of about 75° C. was added to the saponified Marigold oleoresin and stirring was continued for about 10 minutes. The diluted saponified Marigold oleoresin comprising carotenoid crystals was filtered in a buchner funnel to recover the carotenoid crystals. The carotenoid crystals thus obtained were washed with 3600 ml (1:8 volumes calculated to the oleoresin) of hot water maintained at around 75° C. to remove the impurities and bring down the pH of the effluent to neutral around 7.0. The wet crystals were then collected from the filter and dried in a fluid bed drier at a temperature of around 55° C. for 1 hour or until the moisture level is brought to less than 0.3% and the hexane & alcohol levels are less than 10 ppm and 100 ppm respectively.

13.13 g of purified carotenoids crystals rich in T-lutein and T-zeaxanthin were obtained and the physical recovery of the final product was 2.92%. The carotenoid crystals thus obtained contained 91.43% total carotenoids determined by UV-Visible spectrophotometer of which 47.45% was all T-lutein, 46.25% all T-zeaxanthin, 0.85% beta-cryptoxanthin, and 4.28% of beta-carotene, 0.25% of cis-luteins and 0.25% of chrysanthemaxanthin, determined by HPLC.

The carotenoids crystals thus obtained contain 43.38% of T-lutein by weight and 42.28% by weight of T-zeaxanthin with the ratio of T-lutein to T-zeaxanthin by weight to be at about 1:1 ratio (1.02).

The carotenoid crystals thus obtained contained 8.52% of wax content when measured using Gas Chromatography. The carotenoids chemical recovery of the final product was 52.03% with a Lutein chemical recovery of 58.3% and a zeaxanthin chemical recovery of 74.2%. The final product contained a moisture content of 0.30% with 15.38 ppm of ethanol and 8.4 ppm of hexanes detected by Gas chromatography.

EXAMPLE 8

80 kg of lutein rich Marigold meal having 8.99 gm/Kg (0.89%) of total carotenoids (with a carotenoids profile of 74.58% trans-lutein (T-lutein), 4.28% trans-zeaxanthin, 1.94% of beta-carotene, 1.02% of cryptoxanthin and 18.08% cis-isomers & epoxides measured by HPLC) was taken in a 1

KL capacity extractor with circulation facility. 480 Liters of Food grade hexane with a Gas chromatographic purity of more than 98%, was added to the extractor and circulated. The temperature was raised to around 55° C. and maintained for 1 hour, under circulation. After 1 hour the extract was drained and collected in a miscela tank. The extraction was repeated for two more times each with 480 Liters of Hexane under the same conditions of temperature and time. The extracts obtained were collected in the miscela tank. The fourth and fifth extractions were carried out using 400 Liters of hexane in each extraction under circulation and at a temperature of about 58° C. 2084 Liters of miscela collected from the five extractions was taken to an evaporator, preferably a falling film evaporator or a wiped film evaporator to obtain a concentrated miscela containing 70% solids and 30% solvent. The concentrated miscela was distilled further in a distillation unit under atmospheric pressure to increase the concentration of solids to 95% with a solvent level of around 5%. The solvent was distilled further under reduced pressure (450 to 600 mm Hg) to reduce the solvent level further to less than 1%. The total amount of solvent recovered was 1916 Liters with a gas chromatographic purity of more than 98%. 6.728 kg of oleoresin containing 103.83 g/kg of carotenoids (10.38% carotenoids) was obtained with a carotenoids chemical recovery of 97.13%. The oleoresin thus obtained exhibited a carotenoids profile containing 73.9% trans-lutein, 5.89% T-zeaxanthin, 1.34% of betacarotene, 0.52% of cryptoxanthin and 18.35% of cis-isomers/epoxides measured by HPLC.

6.3 kg of lutein rich Marigold oleoresin obtained above containing 103.8 g/kg of carotenoids (10.38% carotenoids) was homogenized for 10 minutes in a 100 Liters capacity reactor under continuous stirring at a temperature of about 40° C. maintained by hot water circulation in the jacket. Alcoholic KOH was prepared by taking 1.26 kg of KOH (20% calculated to the input Oleoresin) with the purity of around 90% and dissolving it in 9.4 Liters (1:1.5 w/v to the Oleoresin) of ethanol. The prepared alcoholic KOH was slowly added into reaction vessel containing the homogenized Marigold oleoresin. The saponification reaction was carried out at a temperature of about 75° C. for 30 minutes. After ensuring the degree of saponification to be more than 99% by HPLC, 25.2 Liters of demineralised hot water (1:4 volumes is the ratio of the oleoresin to water which corresponds to about 1:1.4 volumes calculated to ratio of the reaction mixture to water) maintained at a temperature of 75° C. was added to the saponified Marigold oleoresin and stirring was continued for 10 minutes. The diluted Saponified Marigold oleoresin comprising carotenoid crystals was filtered through filter press, to recover the carotenoid crystals. The carotenoid crystals thus obtained were washed with 50.4 Liters (1:8 w/v calculated to the oleoresin) of hot water maintained at around 75° C. to remove the impurities and bring down the pH of the effluent to neutral around 7.0. The wet crystals were then collected from the filter and dried in a Fluid bed drier at a temperature of around 55° C. for 1 hour or until the moisture level is brought to less than 0.3% and the hexane and alcohol levels are less than 10 ppm and 100 ppm respectively.

520.8 g of purified carotenoids crystals rich in T-lutein were obtained and the physical recovery of the final product was 8.26%. The carotenoid crystals thus obtained contained 90.72% total carotenoids determined by UV-Visible spectrophotometer of which 93.02% was all T-Lutein, 6.21% all T-zeaxanthin, 0.18% of cis-Luteins, 0.18 of betacarotene and 0.41% of cryptoxanthin determined by HPLC. The chemical recovery of the final product is 72.25% of Total carotenoids.

EXAMPLE 9

20 kg of zeaxanthin rich Marigold meal (obtained from Ball Horticulture Inc covered by the U.S. Pat. No. 6,784,351) having 3.29 g/kg (0.329%) of total carotenoids with a carotenoid profile of 59.08% T-zeaxanthin, 14.80% of betacarotene, 11.77% of T-lutein, 2.76% of alpha-cryptoxanthin, 2.33% of beta-cryptoxanthin, 1.98% of alpha-carotene, 0.82% of cis-Lutein, 0.22% of chrysanthemaxanthin and 6.24% of other unidentified carotenoids, measured by HPLC was taken in a 200 Liters capacity extractor with circulation facility. 120 Liters of Food grade hexane with a Gas chromatographic purity of more than 98%, was added to the extractor and circulated. The temperature was raised to about 45° C. and maintained for 1 hour under circulation. After 1 hour, the extract was drained and collected in a miscella tank. The extraction was repeated for 3 more times with 60 Liters of Hexane under the same conditions of temperature and time. The extracts obtained were collected in the miscella tank. 252 Liters of miscella collected from the above 4 extractions was taken to an evaporator, preferably a falling film evaporator or a wiped film evaporator to obtain a concentrated miscella containing 70% solids and 30% solvent. The concentrated miscella was distilled further in a distillation unit under atmospheric pressure to increase the concentration of solids to 95% with a solvent level of around 5%. The solvent was distilled further under reduced pressure (450 to 600 mm Hg) to reduce the solvent level further to less than 1%. The total amount of solvent recovered was 224 Liters with Gas chromatographic purity of more than 98%. 1.46 kg of oleoresin containing 42.88 g/kg of total carotenoids (4.28% of total carotenoids) was obtained with a recovery of 95.14%. The zeaxanthin chemical recovery was 87.74%. The oleoresin thus obtained exhibited a carotenoids profile containing 54.47% of T-zeaxanthin, 9.30% of betacarotene, 19.96% of T-lutein, 3.23% of alpha-cryptoxanthin, 1.89% of beta-cryptoxanthin, 2.68% of alpha-carotene, 0% of cis-lutein and 0.12% of chrysanthemaxanthin and 8.35% of other unidentified carotenoids, measured by HPLC.

1.44 kg of Zeaxanthin rich Marigold oleoresin obtained above containing 42.88 g/kg of total carotenoids (4.28% of total carotenoids) was homogenized for around 10 minutes in a 10 liters capacity extractor under continuous stirring at a temperature of about 40° C. maintained by hot water circulation in the jacket. Alcoholic KOH was prepared by taking 288 g of KOH (20% calculated to the input Oleoresin) with the purity of around 90% and dissolving it in 2.16 Liters (1:1.5 w/v to the Oleoresin) of ethanol. The prepared alcoholic KOH was slowly added into reaction vessel containing the homogenized Marigold oleoresin. The saponification reaction was carried out at a temperature of about 75° C. for 30 minutes. After ensuring the degree of saponification to be more than 99% by HPLC, 5.76 Liters of demineralised hot water (1:4 volumes is the ratio of the oleoresin to water which corresponds to about 1:1.4 volumes calculated to ratio of the reaction mixture to water) maintained at a temperature of about 75° C. was added to the saponified Marigold oleoresin and stirring was continued for 10 minutes. The diluted Saponified Marigold oleoresin comprising carotenoid crystals was filtered in a neutch filter to recover the carotenoid crystals. The carotenoid crystals thus obtained were washed with 11.5 liters (1:8 w/v calculated to the oleoresin) of hot water maintained at around 75° C. to remove the impurities and bring down the pH of the effluent to neutral around 7.0. The wet crystals were then collected from the filter and dried in a Fluid bed drier at a temperature of around 55° C. for 1 hour or until the moisture level is brought to less than 0.3% and the hexane and alcohol levels are less than 10 ppm and 100 ppm respectively.

22.17 g of purified carotenoids crystals rich in T-Zeaxanthin were obtained and the physical recovery of the final product was 1.54%. The carotenoid crystals thus obtained contained 75.01% total carotenoids determined by UV-Visible spectrophotometer of which 90.20% was all T-Zeaxanthin, 6.32% all T-Lutein, 0.10% of Chrysanthemaxanthin, 0.62% of Alpha-carotene and 2.78% of beta-carotene and without any traces of cis-luteins and epoxides, determined by HPLC.

The carotenoids crystals thus obtained contain 67.66% of T-Zeaxanthin by weight and 4.74% by weight of T-lutein with a chemical recovery of 26.98% of Total carotenoids.

EXAMPLE 10

The obtained crystals from Example 8 and the crystals obtained from Example 9 are blended in specific ratios in the laboratory mixer blender for 10 minutes or until there is uniformity of color in the final blend. The blended sample is analyzed for its total carotenoids and HPLC profile. All the three blends are blended in the ratio of 10:1 T-Lutein to T-Zeaxanthin by taking different quantities at each blend. The theoretical profile of the 10:1 blend of T-Lutein to T-zeaxanthin would be of 90.21% total carotenoids measured by UV with 90.2% T-Lutein, 8.92% of T-zeaxanthin and with 0.86% of other carotenoids, measured by HPLC.

Blend 1: 240 g of Lutein and 8 g of Zeaxanthin is taken and blended as mentioned above. The carotenoid crystals thus obtained contained 90.26% total carotenoids determined by UV-Visible spectrophotometer of which 89.0% was all T-Lutein, 9.82% all T-Zeaxanthin and 1.18% of beta-carotene and other carotenoids without any traces of cis-luteins and epoxides, determined by HPLC. The obtained ratio in the above blend is 9.06.

Blend 2: 180 g of Lutein and 6 g of Zeaxanthin is taken and blended as mentioned above. The carotenoid crystals obtained in blend 2 contained 90.63% total carotenoids determined by UV-Visible spectrophotometer of which 90.86% was all T-Lutein, 8.03% all T-Zeaxanthin and 1.11% of beta-carotene and other carotenoids without any traces of cis-luteins and epoxides, determined by HPLC. The obtained ratio in the above blend is 11.31.

Blend 3: 90 g of Lutein and 3 g of Zeaxanthin is taken and blended as mentioned above. The carotenoid crystals obtained in blend 3 contained 88.82% total carotenoids determined by UV-Visible spectrophotometer of which 90.61% was all T-Lutein, 8.63% all T-Zeaxanthin and 0.76% of beta-carotene and other carotenoids without any traces of cis-luteins and epoxides, determined by HPLC. The obtained ratio in the above blend is 10.49.

It is evident from the above experiment that the crystal blending after purifying individually results in varied ratios like 9.06, 11.31, and 10.49 when blended in the same ratios. It is also evident that the recoveries of zeaxanthin purified crystals obtained above is very low as 26.98% which is not economical on a commercial scale.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A process for isolation of carotenoids crystals consisting essentially of trans-lutein and trans-zeaxanthin in a weight ratio of about 10:1, said process comprising:
   contacting a plant source rich in lutein with hexane and extracting at a temperature of about 40° C. to 60° C. to obtain an oleoresin rich in lutein;
   contacting a plant source rich in zeaxanthin with hexane and extracting at a temperature of about 40° C. to 60° C. to obtain an oleoresin rich in zeaxanthin;
   mixing the oleoresin rich in lutein and the oleoresin rich in zeaxanthin in a ratio ranging from about 80:20 (w/w) to 90:10 (w/w) and homogenizing to obtain a mixed oleoresin;
   hydrolyzing the mixed oleoresin with an alcoholic alkali at a temperature of about 70° C. to 80° C. to obtain a reaction mixture; and
   precipitating carotenoids crystals by adding hot water at a temperature of about 55° C. to 80° C. to the reaction mixture to form a precipitate, the precipitate being carotenoids crystals consisting essentially of trans-lutein and trans-zeaxanthin in a ratio of about 10:1
   wherein rich in lutein comprises more than 65% of lutein and rich in zeaxanthin comprises more than 55% of zeaxanthin.

2. The process as claimed in claim 1, wherein the plant source is selected from the group consisting of Marigold flowers, Marigold petals, fruits of paprika and berries of Chinese wolfberries (*Lycium barbarum*).

3. The process as claimed in claim 1, wherein the alcoholic alkali is selected from the group consisting of ethanolic sodium hydroxide and ethanolic potassium hydroxide.

4. The process as claimed in claim 1, wherein the alcoholic alkali is 10%-30% by weight.

5. The process as claimed in claim 1, wherein ratio of the reaction mixture to hot water is in the range of about 1:1 to 1:1.5 (v/v).

6. A process for isolation of carotenoids crystals consisting essentially of trans-lutein and trans-zeaxanthin in a ratio of about 5:1, said process comprising:
   contacting a plant source rich in lutein with hexane and extracting at a temperature of about 40° C. to 60° C. to obtain an oleoresin rich in lutein;
   contacting a plant source rich in zeaxanthin with hexane and extracting at a temperature of about 40° C. to 60° C. to obtain an oleoresin rich in zeaxanthin;
   mixing the oleoresin rich in lutein and the oleoresin rich in zeaxanthin in a ratio ranging from about 70:30 (w/w) to 30:70 (w/w) and homogenizing to obtain a mixed oleoresin;
   hydrolyzing the mixed oleoresin with an alcoholic alkali at a temperature of about 70° C. to 80° C. to obtain a reaction mixture; and
   precipitating carotenoids crystals by adding hot water at a temperature of about 55° C. to 80° C. to the reaction mixture to form a precipitate, the precipitate being carotenoids crystals consisting essentially of trans-lutein and trans-zeaxanthin in a ratio of about 5:1
   wherein rich in lutein comprises more than 65% of lutein and rich in zeaxanthin comprises more than 55% of zeaxanthin.

7. The process as claimed in claim 6, wherein the plant source is selected from the group consisting of Marigold flowers, Marigold petals, fruits of paprika and berries of Chinese wolfberries (*Lycium barbarum*).

8. The process as claimed in claim 6, wherein the alcoholic alkali is selected from the group consisting of ethanolic sodium hydroxide and ethanolic potassium hydroxide.

9. The process as claimed in claim 6, wherein the alcoholic alkali is 10%-30% by weight.

10. The process as claimed in claim 6, wherein ratio of the reaction mixture to hot water is in the range of about 1:1 to 1:1.5 (v/v).

11. A process for isolation of carotenoids crystals consisting essentially of trans-lutein and trans-zeaxanthin in a ratio of about 1:1, said process comprising:
   contacting a plant source rich in lutein with hexane and extracting at a temperature of about 40° C. to 60° C. to obtain an oleoresin rich in lutein;
   contacting a plant source rich in zeaxanthin with hexane and extracting at a temperature of about 40° C. to 60° C. to obtain an oleoresin rich in zeaxanthin;
   mixing the oleoresin rich in lutein and the oleoresin rich in zeaxanthin in a ratio ranging from about 10:90 (w/w) to 20:80 (w/w) and homogenizing to obtain a mixed oleoresin;
   hydrolyzing the mixed oleoresin with an alcoholic alkali at a temperature of about 70° C. to 80° C. to obtain a reaction mixture; and
   precipitating carotenoids crystals by adding hot water at a temperature of about 55° C. to 80° C. to the reaction mixture to form a precipitate
   the precipitate being carotenoids crystals consisting essentially of trans-lutein and trans-zeaxanthin in a ratio of about 1:1
   wherein rich in lutein comprises more than 65% of lutein and rich in zeaxanthin comprises more than 55% of zeaxanthin.

12. The process as claimed in claim 11, wherein the plant source is selected from the group consisting of Marigold flowers, Marigold petals, fruits of paprika and berries of Chinese wolfberries (*Lycium barbarum*).

13. The process as claimed in claim 11, wherein the alcoholic alkali is selected from the group consisting of ethanolic sodium hydroxide and ethanolic potassium hydroxide.

14. The process as claimed in claim 11, wherein ratio of the reaction mixture to hot water is in the range of about 1:1 to 1:1.5 (v/v).

15. The process as claimed in claim 1 wherein the reaction mixture is maintained at a temperature of about 70-80° C. for 30 minutes to complete the saponification.

16. The process as claimed in claim 6 wherein the reaction mixture is maintained at a temperature of about 70-80° C. for 30 minutes to complete the saponification.

17. The process as claimed in claim 11 wherein the reaction mixture is maintained at a temperature of about 70-80° C. for 30 minutes to complete the saponification.

* * * * *